(12) United States Patent
Gysling et al.

(10) Patent No.: US 7,343,820 B2
(45) Date of Patent: Mar. 18, 2008

(54) APPARATUS AND METHOD FOR FISCAL MEASURING OF AN AERATED FLUID

(75) Inventors: Daniel L. Gysling, Glastonbury, CT (US); Douglas H. Loose, Southington, CT (US)

(73) Assignee: CiDRA Corporation, Wallingford, CT (US)

( * ) Notice: Subject to any disclaimer, the term of this patent is extended or adjusted under 35 U.S.C. 154(b) by 65 days.

(21) Appl. No.: 11/442,953

(22) Filed: May 30, 2006

(65) Prior Publication Data
US 2006/0266127 A1 Nov. 30, 2006

Related U.S. Application Data (60) Provisional application No. 60/736,684, filed on Nov. 14, 2005, provisional application No. 60/685,532, filed on May 27, 2005.

(51) Int. Cl.
*G01F 1/32* (2006.01)
(52) U.S. Cl. .................................. 73/861.23
(58) Field of Classification Search ............... 73/53.03, 73/861.42, 861.25, 861.23, 61.49; 702/23
See application file for complete search history.

(56) References Cited

U.S. PATENT DOCUMENTS

| | | | |
|---|---|---|---|
| 6,354,147 B1 | 3/2002 | Gysling et al. | |
| 6,435,030 B1 | 8/2002 | Gysling et al. | |
| 6,450,037 B1 | 9/2002 | McGuinn et al. | |
| 6,463,813 B1 | 10/2002 | Gysling et al. | |
| 6,536,291 B1 | 3/2003 | Gysling et al. | |
| 6,587,798 B2 | 7/2003 | Kersey et al. | |
| 6,601,458 B1 | 8/2003 | Gysling et al. | |
| 6,609,069 B2 | 8/2003 | Gysling et al. | |
| 6,691,584 B2 | 2/2004 | Gysling et al. | |
| 6,698,297 B2 | 3/2004 | Gysling et al. | |
| 6,732,575 B2 | 5/2004 | Gysling et al. | |

(Continued)

FOREIGN PATENT DOCUMENTS

DE  19710296  3/1988

(Continued)

OTHER PUBLICATIONS

Sonar-Based Volumetric Flow Meter for Pulp and Paper Applications—By: Daniel L. Gysling & Douglas H. Loose—Dec. 3, 2002.

(Continued)

*Primary Examiner*—Jewel Thompson
(74) *Attorney, Agent, or Firm*—Michael Grillo (57) ABSTRACT

A method and apparatus for performing a fiscal measurement of at least one characteristic of an aerated fluid flowing within a pipe is provided, wherein the apparatus includes at least one metering device for determining the mixture density of the fluid, the speed of sound of the fluid and the speed of sound of the liquid portion of the fluid, wherein the at least one metering device generates meter data responsive to the mixture density of the fluid, the speed of sound of the fluid and the speed of sound of the liquid portion of the fluid. The apparatus further includes a processing device communicated with the at least one metering device, wherein the processing device receives the meter data and processes the meter data to generate the at least one fiscal measurement.

18 Claims, 7 Drawing Sheets

U.S. PATENT DOCUMENTS

| | | | |
|---|---|---|---|
| 6,782,150 B2 | 8/2004 | Davis et al. | |
| 6,813,962 B2 | 11/2004 | Gysling et al. | |
| 6,837,098 B2 | 1/2005 | Gysling et al. | |
| 6,862,920 B2 | 3/2005 | Gysling et al. | |
| 6,889,562 B2 | 5/2005 | Gysling et al. | |
| 6,898,541 B2 | 5/2005 | Gysling et al. | |
| 6,959,604 B2 | 11/2005 | Bryant et al. | |
| 6,971,259 B2 | 12/2005 | Gysling | |
| 6,988,411 B2 | 1/2006 | Gysling et al. | |
| 7,058,549 B2 | 6/2006 | Gysling et al. | |
| 7,062,976 B2 | 6/2006 | Gysling et al. | |
| 7,086,278 B2 | 8/2006 | Gysling et al. | |
| 7,096,719 B2 | 8/2006 | Gysling et al. | |
| 7,110,893 B2 | 9/2006 | Loose et al. | |
| 7,121,152 B2 | 10/2006 | Winston et al. | |
| 7,127,360 B2 | 10/2006 | Gysling et al. | |
| 7,134,320 B2 * | 11/2006 | Gysling et al. | 73/32 A |
| 7,139,667 B2 | 11/2006 | Rothman et al. | |
| 7,152,460 B2 | 12/2006 | Gysling et al. | |
| 7,197,403 B2 * | 3/2007 | Morrow et al. | 702/27 |
| 2003/0089161 A1 | 5/2003 | Gysling | |
| 2003/0136186 A1 | 7/2003 | Gysling | |
| 2003/0154036 A1 | 8/2003 | Gysling et al. | |
| 2004/0016284 A1 | 1/2004 | Gysling et al. | |
| 2004/0069069 A1 | 4/2004 | Croteau | |
| 2004/0074312 A1 | 4/2004 | Gysling et al. | |
| 2004/0144182 A1 | 7/2004 | Gysling et al. | |
| 2004/0168522 A1 | 9/2004 | Bailey et al. | |
| 2004/0168523 A1 | 9/2004 | Bailey et al. | |
| 2004/0199340 A1 | 10/2004 | Gysling et al. | |
| 2004/0255695 A1 | 12/2004 | Gysling et al. | |
| 2005/0005711 A1 | 1/2005 | Curry et al. | |
| 2005/0005912 A1 | 1/2005 | Gylsing et al. | |
| 2005/0011258 A1 | 1/2005 | Didden et al. | |
| 2005/0011283 A1 | 1/2005 | Gysling et al. | |
| 2005/0012935 A1 | 1/2005 | Kersey | |
| 2005/0050956 A1 | 3/2005 | Croteau et al. | |
| 2005/0061060 A1 | 3/2005 | Gysling et al. | |
| 2005/0125170 A1 | 6/2005 | Gysling | |
| 2005/0246111 A1 | 11/2005 | Gysling et al. | |
| 2006/0000287 A1 * | 1/2006 | Arai et al. | 73/703 |
| 2006/0037385 A1 | 2/2006 | Gysling | |
| 2006/0048583 A1 | 3/2006 | Gysling | |
| 2006/0053809 A1 | 3/2006 | Gysling et al. | |
| 2006/0169058 A1 | 8/2006 | Gysling | |
| 2007/0001028 A1 | 1/2007 | Gysling | |
| 2007/0006744 A1 | 1/2007 | Gysling | |

FOREIGN PATENT DOCUMENTS

| | | |
|---|---|---|
| EP | 1 186 868 | 3/2002 |
| GB | 2 282 931 | 4/1995 |
| WO | WO 93/14382 | 7/1993 |
| WO | WO 99/67629 | 12/1999 |
| WO | WO 00/60317 | 10/2000 |
| WO | WO 01/02810 | 1/2001 |
| WO | WO 2004068080 | 9/2004 |

OTHER PUBLICATIONS

Sonar Based Volumetric Flow Meter for Chemical and Petrochemical Applications—By: Daniel L. Gysling & Douglas H. Loose—Feb. 14, 2003.
Sonar Based Volumetric Flow and Entrained Air Measurement for Pulp and Paper Applications—By: Daniel L. Gysling & Douglas H. Loose—Jan. 24, 2003.
"Flow Velocity Measurement using Spatial Filter" By: Yoshio Kurita, Takaharu Matsumoto and Yukitake Shibata , Nov. 1979.
"New Flowmeter Principle"—By: Walt Boyes—Published in Flow Control Magazine—Oct. 2003 Issue.
"Piezoelectric Polymers"—By: J.S. Harrison and Z. Ounaies—ICASE Report.
Piezo Film Sensors Technical Manual—Measurement Specialities, Inc. Apr. 2, 1999.
Mass Fraction Measurements in Multiphase Flows using a Clamp-on PVDF Array—Johan Carlson, IEEE Ultrasonics Symposium Proceedings, vol. 1, Apr. 18, 2001, pp. 471-474.
"Noise and Vibration Control Engineering Principles and Applications", Leo L. Beranek and Istvan L. Ver, A. Wiley Interscience Publication, pp. 537-541, Aug. 1992.
"Two Decades of Array Signal Processing Research", The Parametric Approach, H. Krim and M. Viberg, IEEE Signal Processing Magazine, Jul. 1996, pp. 67-94.
"Development of an array of pressure sensors with PVDF film, Experiments in Fluids 26", Jan. 8, 1999, Springer-Verlag.
"Viscous Attentuation of Acoustic Waves in Suspensions" by R.L. Gibson, Jr. and M.N. Toksoz, 1989 Acoustical Society of America, May 1989, pp. 1925-1934.

* cited by examiner

APPARATUS AND METHOD FOR FISCAL MEASURING OF AN AERATED FLUID

CROSS-REFERENCE TO RELATED PATENT APPLICATIONS

The present application is related to and claims priority of U.S. Provisional Patent Application No. 60/685,532, filed May 27, 2005 and U.S. Provisional Patent Application No. 60/736,684, filed Nov. 14, 2005, which are incorporated by reference herein in their entireties.

TECHNICAL FIELD

The present invention relates generally to a method and apparatus for measuring at least one characteristic of an aerated fluid, and more particularly to a method and apparatus for providing a fiscal measurement of the liquid and/or solid portion of a flowing aerated fluid.

BACKGROUND OF THE INVENTION

It is a well known concept that the presence of entrained gases within a flowing fluid impairs the ability of most known volumetric flow meters to accurately measure the liquid volume of the flowing fluid. In fact, the effect of these entrained gases typically results in an over-reporting of the liquid component flow rates by an amount equal to the volume of the entrained gases. As such, most standards for measuring the fiscal volumetric flow of liquids require that the liquid be completely devoid of entrained gases. A problem arises, however, when it becomes impractical to ensure that the liquid stream in question is indeed, completely devoid of free gases. Although typically less than 1% of the volume, these gas volume fraction levels can often be the primary source of error in fiscal measurement and currently, except for eliminating the entrained gases altogether, there are no other solutions available to account for errors in the fiscal measurement of liquids with entrained gases. Unfortunately, in many cases, this is not a practical solution.

This problem is of particular interest in the petroleum industry in which billions of dollars of crude oil is fiscally measured each day on its way from the well heads to the refineries. Due to the large amounts of light hydrocarbons present in crude, crude oils have historically demonstrated a propensity to "out gas" during transport, resulting in small, but unknown levels of entrained gases sometimes being present at fiscal measurement locations. Since most fiscal transactions of liquids are based on the amount of liquid, current fiscal measurement standards applied to liquids with entrained gases will result in an over-reporting of the liquid flow rate. It should be appreciated that this over-reporting of liquids applies to all known measurement devices and currently, it is believed that there exists no commercial methods for providing accurate fiscal volumetric flow measurements of slightly aerated mixtures. Although the preferred solution to addressing the disadvantages discussed hereinabove would be to completely de-aerate the liquids prior to measurement, this solution appears to be impractical.

SUMMARY OF THE INVENTION

An apparatus for performing a fiscal measurement of at least one characteristic of an aerated fluid flowing within a pipe is provided, wherein the apparatus includes at least one metering device for determining the mixture density of the fluid, the speed of sound of the fluid and the speed of sound of the liquid portion of the fluid and wherein the at least one metering device generates meter data responsive to the mixture density of the fluid, the speed of sound of the fluid and the speed of sound of the liquid portion of the fluid. A processing device is also provided, wherein the processing device is communicated with the at least one metering device, wherein the processing device receives the meter data and processes the meter data to generate the at least one fiscal measurement.

A method for determining a fiscal measurement of at least one characteristic of an aerated fluid flowing within a pipe is provided, wherein the method includes receiving sensor data responsive to the mixture density of the fluid, the speed of sound of the fluid, the speed of sound of the liquid portion of the fluid and the volumetric flow rate of the fluid flowing within the pipe. Additionally, the sensor data is processed to generate the fiscal measurement of the at least one characteristic of the aerated fluid flowing within the pipe.

BRIEF DESCRIPTION OF THE DRAWINGS

The foregoing and other features and advantages of the present invention will be more fully understood from the following detailed description of illustrative embodiments, taken in conjunction with the accompanying drawings in which like elements are numbered alike.

DETAILED DESCRIPTION OF THE INVENTION

Figure 1A:
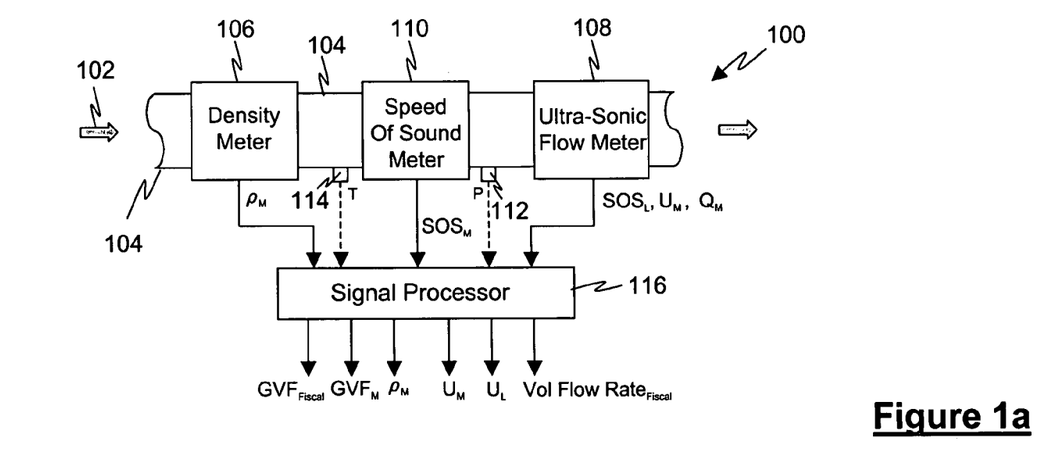
FIG. 1a is a schematic illustration of an apparatus for fiscally measuring an aerated mixture flowing in a pipe, in accordance with an exemplary embodiment.

It should be appreciated that there are at least two ways to address the disadvantages discussed hereinabove. One way would involve ensuring that the liquids being measured are completely devoid of free gases and another way would involve being able to accurately measure the volumetric flow of slightly aerated liquid-continuous streams. In accordance with the present invention, a meter that measures the speed of sound within a mixture in combination with any well-known fiscal measurement device is provided by installing a speed of sound meter (e.g., a sonar-based gas volume fraction meter either upstream and/or downstream of the fiscal measurement device. The speed of sound meter provides an indication of when entrained gases are present in the mixture. By monitoring the speed of sound of the liquid ($SoS_L$) under measurement for entrained gases, the sonar-based meter can provide verification that the liquid flow is devoid, to some threshold level, of free gas. When the level of the measured entrained gas exceeds a predetermined threshold, a signal may be provided to the user indicating that, due to the increased level of entrained gas, the well-known fiscal measurement device may not be providing an accurate measurement of the volumetric flow rate of the mixture within a predetermined range. As illustrated in FIG. 1a, another way would involve utilizing the speed of sound measurement within the mixture ($SoS_M$) to provide a fiscal measurement of the aerated mixture above and below the above referenced predetermined threshold.

Referring to FIG. 1a, one embodiment of an apparatus 100 for fiscally measuring a mixture 102 (comprising an aerated liquid mixture and/or an aerated liquid/solid mixture) flowing within a pipe, duct, channel, conduit, or the like (hereinafter "pipe") 104 is shown. As described in further detail hereinafter, the apparatus 100 combines at least three separate, compositional measurements of the mixture 102 to provide a real time fiscal measurement of the volumetric flow rate of an aerated mixture 102. It should be appreciated that a "fiscal" measurement is one that provides an accurate measurement of the desired portion of the mixture. For example, a fiscal measurement of the volumetric flow rate of the mixture 102 is a measurement of only the liquid or solid portion of the mixture 102, excluding the volumetric flow of any entrained gases.

As shown, the apparatus 100 includes a first device 106, a second device 108 and a third device 110. The first device 106 senses at least one first device parameter of the mixture 102 and generates a signal indicative of the at least one first device parameter, wherein the at least one first device parameter of the mixture 102 is responsive to the density ($\rho_{mix}$) of the mixture 102. The second device 108 senses at least one second device parameter of the mixture 102 and generates a signal indicative of the at least one second device parameter, wherein the at least one second device parameter is responsive to the velocity of the mixture (or volumetric flow rate of the mixture 102) and the Speed of Sound ($SoS_L$) propagating through the liquid and/or solid portion of the mixture 102. In a similar fashion, the third device 110 senses at least one third device parameter of the mixture 102 and generates a signal indicative of the at least one third device parameter, wherein the at least one third device parameter is responsive to the Speed of Sound ($SoS_M$) through the mixture 102. Additionally, a pressure sensor 112 and a temperature sensor 114 may be provided to provide the pressure and temperature, respectively, of the mixture 102. Furthermore, the apparatus 100 may include a signal processor 116 that receives signals from each of the first device 106, second device 108 and third device 110 and, using the input from these devices 106, 108, 110, determines a fiscal volumetric flow rate, a fiscal gas volume fraction, a density ($\rho_{mix}$) of the mixture 102, a mixture velocity and a liquid velocity.

It should be appreciated that each of the first device 106, the second device 108 and the third device 110 senses a different parameter of the mixture 102. The first device 106 senses any parameter of the mixture 102 that indicates the density ($\rho_{mix}$) of the mixture 102. For example, the first device 106 may include a Coriolis meter, which senses mass loading of vibrating tubes through which the mixture 102 flows, and characterizes the aeroelastic response of the fluid-filled, vibrating tubes to determine the density of the mixture 102 flowing through the tubes. It should be appreciated that the Coriolis meter may be any known Coriolis meter suitable to the desired end purpose, such as a two inch bent tube Coriolis meter manufactured by MicroMotion Inc. and/or a two in straight tube Coriolis meter manufactured by Endress & Hauser Inc. Alternatively, devices other than a Coriolis meter may be used to determine the density ($\rho_{mix}$) of the mixture 102. For example, a gamma (radiation) densitometer, which senses the absorption of radiation by the mixture, may be used as the first device 106. One will appreciate that the present invention contemplates that any device that measures density of the mixture may be used.

Figure 1B:
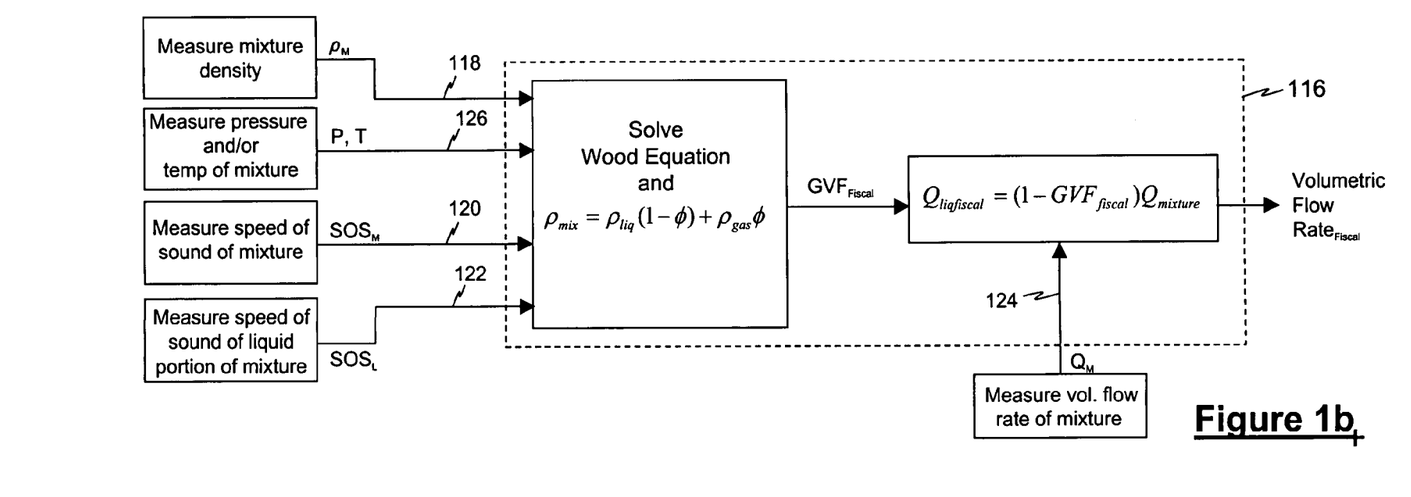
FIG. 1b is a functional block diagram of the apparatus of FIG. 1.
Figure 1C:
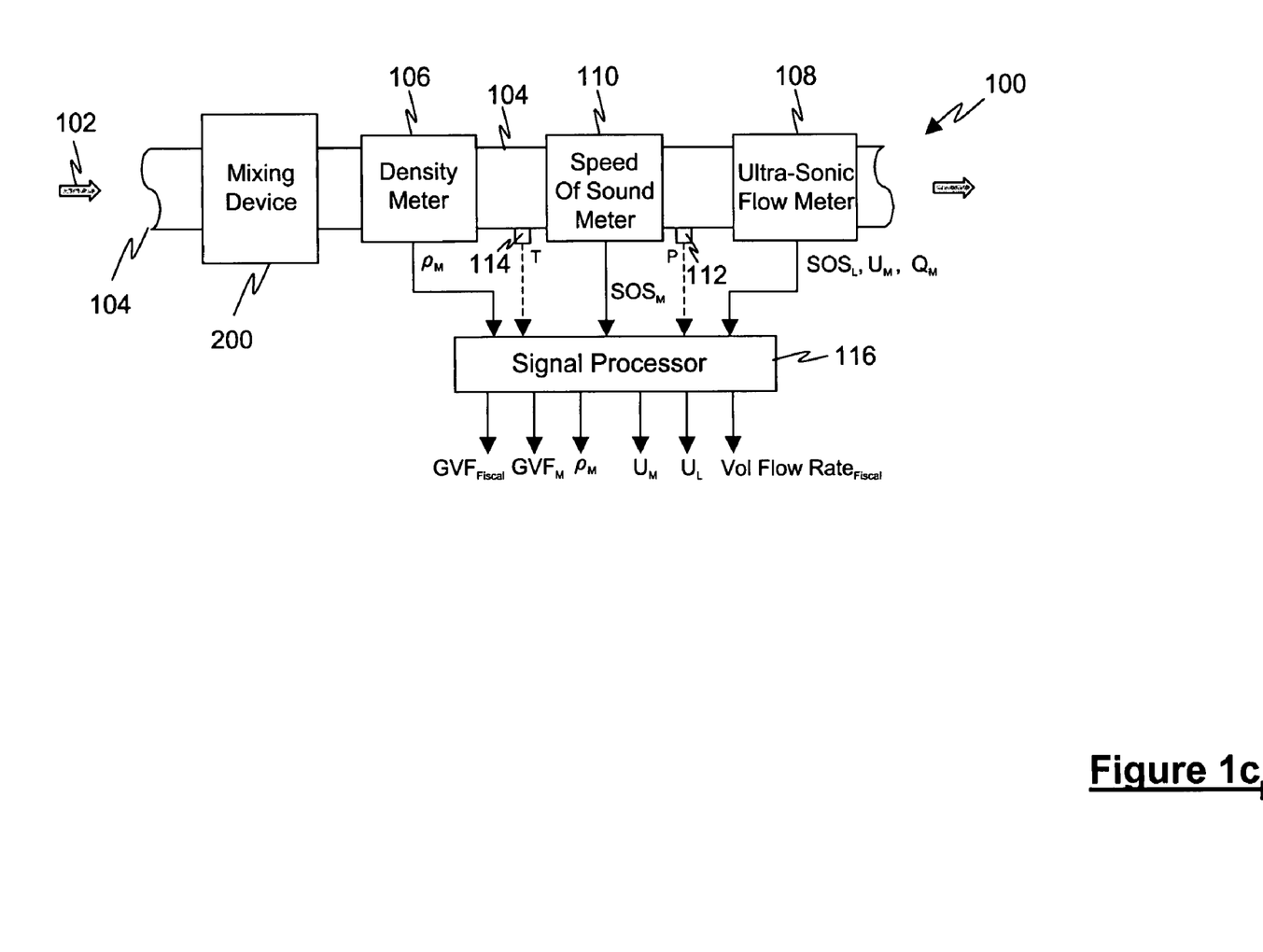
FIG. 1c is a schematic illustration of an apparatus for fiscally measuring an aerated mixture flowing in a pipe, in accordance with an additional embodiment.

Referring to FIG. 1c, optionally at least one mixing device 200 may be included with the apparatus 100. The mixing device 200 may be associated with the fluid 102 flowing within the pipe 104 for mixing the fluid 102 to prevent slippage from occurring, wherein slippage may be viewed as the difference of the flow rate between the bubble portion of the fluid (i.e. gas portion) and the liquid portion of the fluid, such as may occur with the presence of larger gas bubbles, stratified flows and pipes that are vertically positioned (where gravity contributes to slippage). Mixing the fluid prior to measurement may reduce and/or eliminate the difference in the flow rate between the bubble portion of the fluid (i.e. gas portion) and the liquid portion of the fluid and thus allow for a more accurate flow rate determination. It should be appreciated that any mixing method and/or mixing device 200 suitable to the desired end purpose may be used to mix the fluid. Additionally, it should be appreciated that where more than one metering device is used, the mixing device 200 may be disposed prior to all of the metering devices or the mixing device may be disposed between metering devices.

In the embodiment of FIG. 1a, the second device 108 may measure the speed of sound ($SoS_M$) propagating through the liquid and/or liquid/solid portion of the mixture 102 and may also measure the velocity and/or volumetric flow rate of the aerated mixture 102. For example, the second device 108 may be an ultra-sonic volumetric flow meter that determines the volumetric flow rate and velocity of the mixture 102. In addition, the ultra-sonic flow meter may be used to measure the speed of sound ($SoS_L$) propagating through the liquid and/or liquid/solid portion of the mixture 102, which will be described in greater detail hereinafter. One will appreciate that the present invention contemplates that any device may be used to measure the $SoS_L$ and the volumetric flow rate of the mixture 102. While the $SoS_L$ and volumetric flow rate are described as being measured by a single device, it should be appreciate that multiple (such as two) separate devices may be used for each function. For example, at least one ultra-sonic sensor may be used to measure the $SoS_L$ and any known volumetric flow meter, such as a magmeter and others, may be used to measure the volumetric flow rate of the mixture 102.

The third device 110 measures the speed of sound ($SoS_M$) propagating through the mixture 102. For example, the third device 110 may include a Gas Volume Fraction (GVF) meter that employs a sensing device having a plurality of strain-based or pressure sensors spaced axially along the pipe 104 for measuring the acoustic pressures propagating through the mixture 102. The GVF meter may calculate the GVF of the mixture 102 using the measured speed of sound ($SoS_M$) of the mixture 102, as described in further detail hereinafter. Additionally, the GVF meter may also use the pressure of the process flow to determine the GVF, wherein the pressure may be a measured value or an estimated value. It should be appreciated that the GVF meter is similar to that described in U.S. patent application Ser. No. 10/762,410 filed Jan. 21, 2004, which is incorporated in its entirety herein by reference. One will also appreciate that the present invention contemplates that any device that measures the speed of sound ($SOS_M$) propagating through the mixture 102 may be used.

Problematically, the inclusion of entrained air or other gasses into the mixture may result in measurement errors in the volumetric flow rate measurement. For example, the void fraction of the air within the pipe 104 can cause errors in density and flow rate measurements. For Coriolis meters, some of the fundamental assumptions regarding the interaction of the fluid and the structure can deteriorate under different operating conditions. Specifically, aerated fluids in oscillating tubes behave differently from single phase fluids, which results in measurement error. The uncertainty resulting from such measurement errors prevent the mixture density measurements from being relied upon to determine a unique measurement of the volumetric flow rate when entrained gases are present in the mixture 102. As a solution to this, the microprocessor of FIG. 1a combines three different compositional measurements simultaneously (or almost simultaneously) to provide a real time (or almost real time) fiscal volumetric flow rate for aerated mixtures.

Referring to FIGS. 1a and 1b, the third device 110 (i.e. the speed of sound meter e.g., a sonar-based gas volume fraction meter) measures the speed at which sound propagates through the mixture 102 along the axis of the pipe 104. The speed of propagation can be viewed as a ratio between the bulk modulus of the mixture 102 (inverse of compressibility) and the density of the mixture 102. Since most gases are orders of magnitude more compressible than most liquids under most conditions, the amount of free gas is strongly correlated to the amount of gas present in a mixture. As such, the relationship between the speed of propagation and the gas volume fraction, and other properties of the pipe 104, the liquid, and the gas phases is given by the Wood Equation. It should be appreciated that the physics of the measurement is such that this approach is highly accurate and robust to variations in liquid phase properties for situations in which the compressibility introduced by the gas is significantly greater that the compressibility of the fluid and that of the pipe 104 itself. These are typically applications in which the gas volume fraction (GVF) is greater that ~0.1%.

Figure 2:
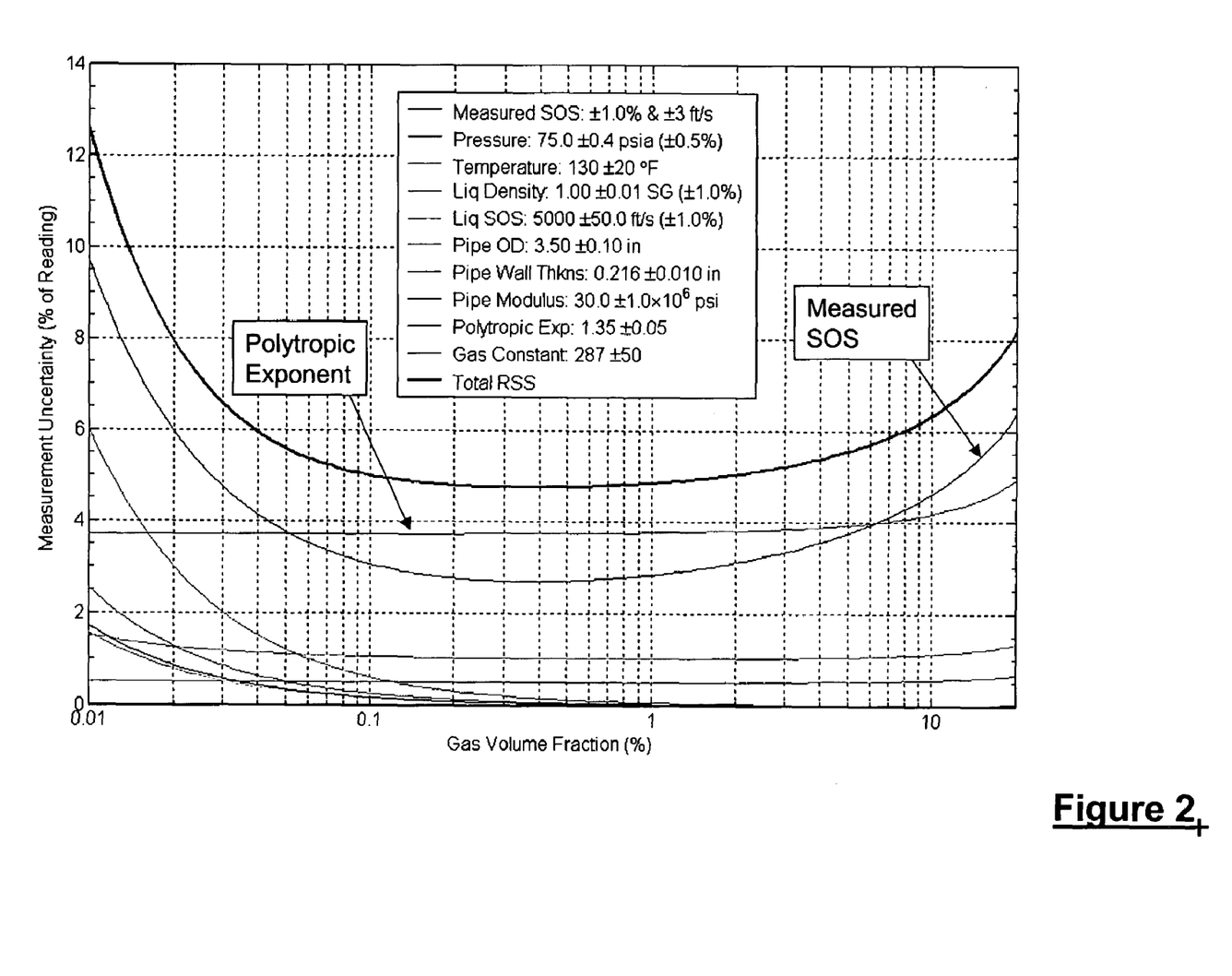
FIG. 2 is a plot depicting the relationship between gas volume fraction of the aerated mixture and the percent uncertainty of a measurement of the volumetric flow of an aerated mixture flowing within a pipe, in accordance with an exemplary embodiment.

Referring to FIG. 2, the relative error of the entrained gas measurement for representative conditions of a gas volume fraction meter 110 is shown. It shows that above approximately 0.1% GVF, there are three main sources of measurement uncertainty: uncertainty in the measured sound speed, the polytropic exponent, and the liquid density. However, below 0.1% GVF, the liquid sound speed begins to play a role in measurement uncertainty as well. The present invention describes a method to provide a highly accurate measurement of gas volume fraction below 1.0% GVF (particularly in the range of 0.01%-0.1%) and subsequently a highly accurate measurement of the volumetric flow of liquid within continuous mixtures. It is assumed that most fiscal measurements are performed on liquids that have relatively low gas volume fraction levels, predominantly in the range of 0.01% to 1.0% GVF. In this range, it is important to have both an accurate measure of the total mixture flow rate (fiscal measurement) and an accurate measure of the gas volume fraction (fiscal measurement) to determine the liquid volumetric flow rate. In order to address this, it is proposed to use a combination of devices, as shown in FIGS. 1a and 1b, to perform these measurements, specifically, an ultrasonic flow meter 108, (either clamp-on or wetted transducer), a coriolis meter 106 for mass and density measurements (preferably provided by the coriolis mass flow meter) and a sonar-based speed of sound meter 110. The combination of these devices (or measurements) provides a practical and novel approach to fiscal-quality volumetric flow measurement of aerated fluids.

As an example, consider the specific combination of a fiscally rated, multiphase ultrasonic meter 108, a fiscally rated coriolis meter 106 and a sonar-based speed of sound meter 110, as shown in FIG. 1a. In the limiting case of no entrained gas, a high accuracy volumetric flow measurement in a standard manner performed by any device with the desired accuracy is known. In this example, the ultrasonic meter 108 and/or the coriolis flow meter 106 is known to provide a fiscal measurement of the volumetric flow measurement. However, with introduction of an entrained gas, a more elaborate collaboration of the devices is required to maintain the desired accuracy, as shown in FIGS. 1a and 1b.

Figure 5:
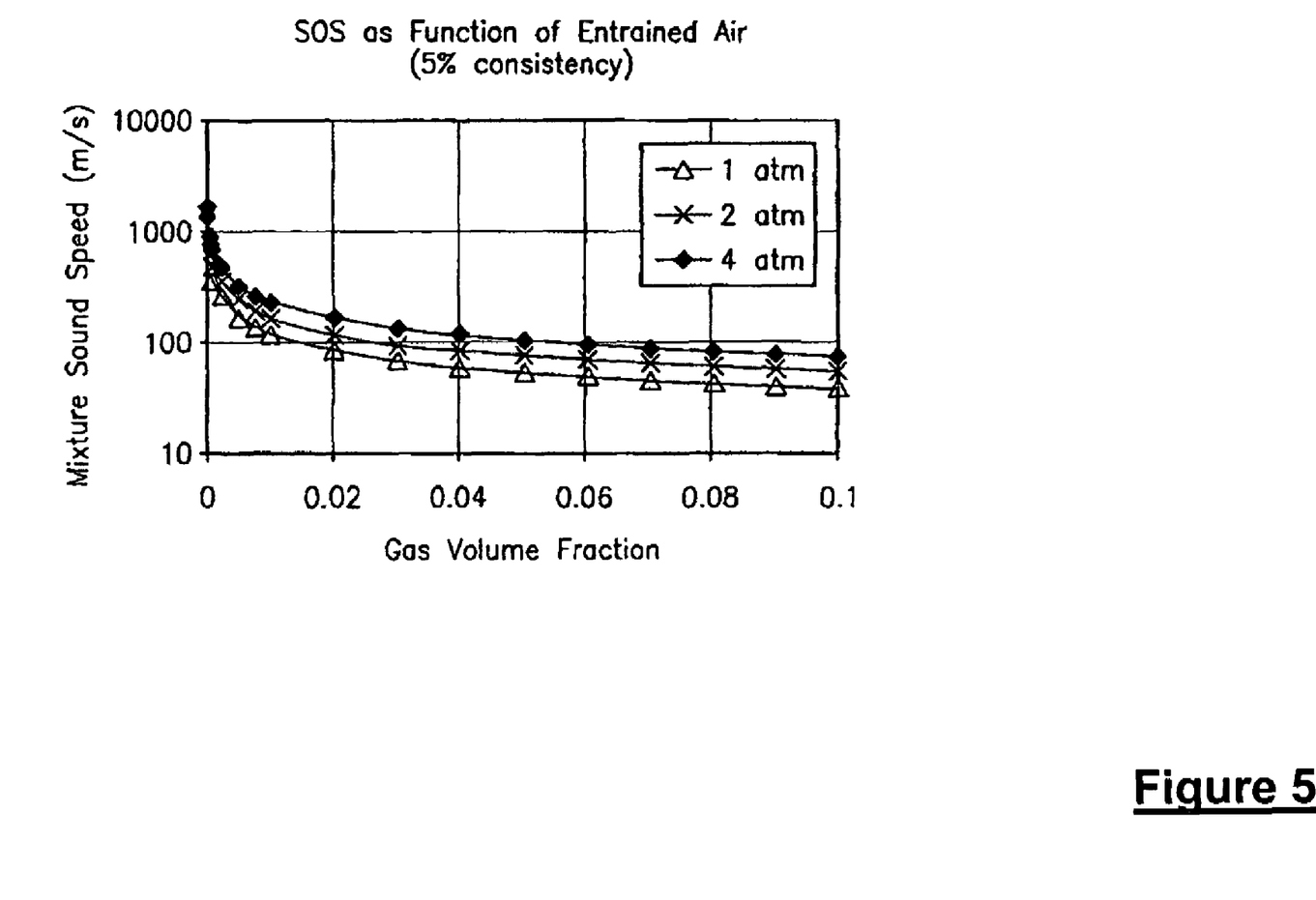
FIG. 5 is a plot of the speed of sound of the fluid flow as a function of the gas volume fraction over a range of different pressures, in accordance with an exemplary embodiment.

Firstly, the presence of gas will be indicated by a difference in the speed of sound reported by the ultrasonic meter 108 and that reported by the sonar-based flow meter 110. The high frequency ultrasonic meter 108 uses short wavelength acoustics whose, although scattered by the gas bubbles, propagation velocity is unaffected by entrained gases and therefore, the ultrasonic meter continues to report liquid phase sound speed ($SOS_L$). On the other hand, the gas volume fraction meter is governed by the Wood equation, and the sonar-based sound speed decreases with the introduction of entrained gas, as shown in FIG. 5. Thus, the divergence of the two measurements is an indication of the presence of entrained gas. However, to accurately determine the amount of gas present, particularly at low gas volume fractions, it is highly desirable to know both the liquid phase sound speed ($SOS_L$) and liquid phase density ($\rho_L$). Vibrating tube density meters (which includes density measurements provided by Coriolis meters) have been shown to continue to accurately report mixture density ($\rho_{mix}$) in the presence of small, well dispersed gas bubbles, such as those expected in this application and the measured (mixture) density ($\rho_{mix}$) is related to the gas volume fraction and gas and liquid densities via the following relationship.

Solving for the gas volume fraction ($\phi$) using the Wood equation (Eqn. 1 below) and the relationship of the mixture density ($\rho_{mix}$) to the gas volume fraction (Eqn. 2 below), the fiscal measurement for the gas volume fraction ($GVF_{fiscal}$) can be determined.

$$a_{MEAS} = \frac{1}{\left\{\left[\phi\frac{P}{RT} + (1-\phi)\rho_L\right]\left(\frac{\phi}{P\gamma} + \frac{(1-\phi)}{\rho_L a_L^2} + \frac{D-t}{Et}\right)\right\}^{0.5}}; \quad \text{(Eqn. 1)}$$

Where:
$a_{MEAS}$=measured sound speed, m/s
$\phi$=gas volume fraction
P=pressure, Pa absolute
T=temperature, deg K
R=gas constant, J/kg-K
$\gamma$=polytropic exponent
$\rho_L$=measured liquid density, kg/m³
$a_L$=measured liquid sound speed, m/s D=pipe outside diameter, m
t=pipe wall thickness, m
E=pipe modulus of elasticity, Pa $$\rho_{mix} = \rho_{liq}(1-\phi) + \rho_{gas}\phi; \quad \text{(Eqn. 2)}$$

Wherein, $\rho_{mix}$ is the measured mixture density, $\rho_{liq}$ is the measured liquid density, $\phi$ is the Gas Volume Fraction and $\rho_{gas}$ is the measured gas density.

Using the above relationship, the knowledge of the mixture sound speed ($SOS_M$) (from the GVF sonar-based sound speed meter 110) and the liquid sound speed ($SOS_L$) (from the ultrasonic meter 108), an accurate measure of the Gas Volume Fraction (GVFfiscal) that is insensitive to variations in liquid phase density ($\rho_L$) and sound speed can be provided, even at low gas volume fraction levels typically found in fiscal applications. Consequently, referring to FIG. 2, the percentage of measured uncertainty of the gas volume fraction between the range of 0.01 and 0.1% GVF is greatly reduced to provide an accurate (fiscal) GVF measurement below 1.0% GVF. As such, the fiscal measurement can then be determined using the following relationship (Eqn. 3 below):

$$Q_{liqfiscal} = (1 - GVF_{fiscal})Q_{mixture}; \quad \text{(Eqn. 3)}$$

where $Q_{liqfiscal}$ is the fiscal measurement of the volumetric flow of the liquid portion (or liquid/solid portion) of the mixture 102 and $Q_{mixture}$ is the measured volumetric flow rate.

Referring again to FIG. 1b, a functional block diagram of the present invention is illustrated, wherein the processor 116 receives a measured mixture density signal 118, a measured speed of sound propagating through the mixture 102 signal 120, a measured speed of sound propagating through the liquid portion of the mixture 102 signal 122, and a measured volumetric flow rate of the mixture 102 signal 124 to determine the fiscal gas volume fraction and the fiscal volumetric flow rate. As shown, a measured pressure and/or temperature signal 126 of the mixture 102 may also be provided. It should be understood that any of these measured parameters may be provided via any known device.

Figure 3A:
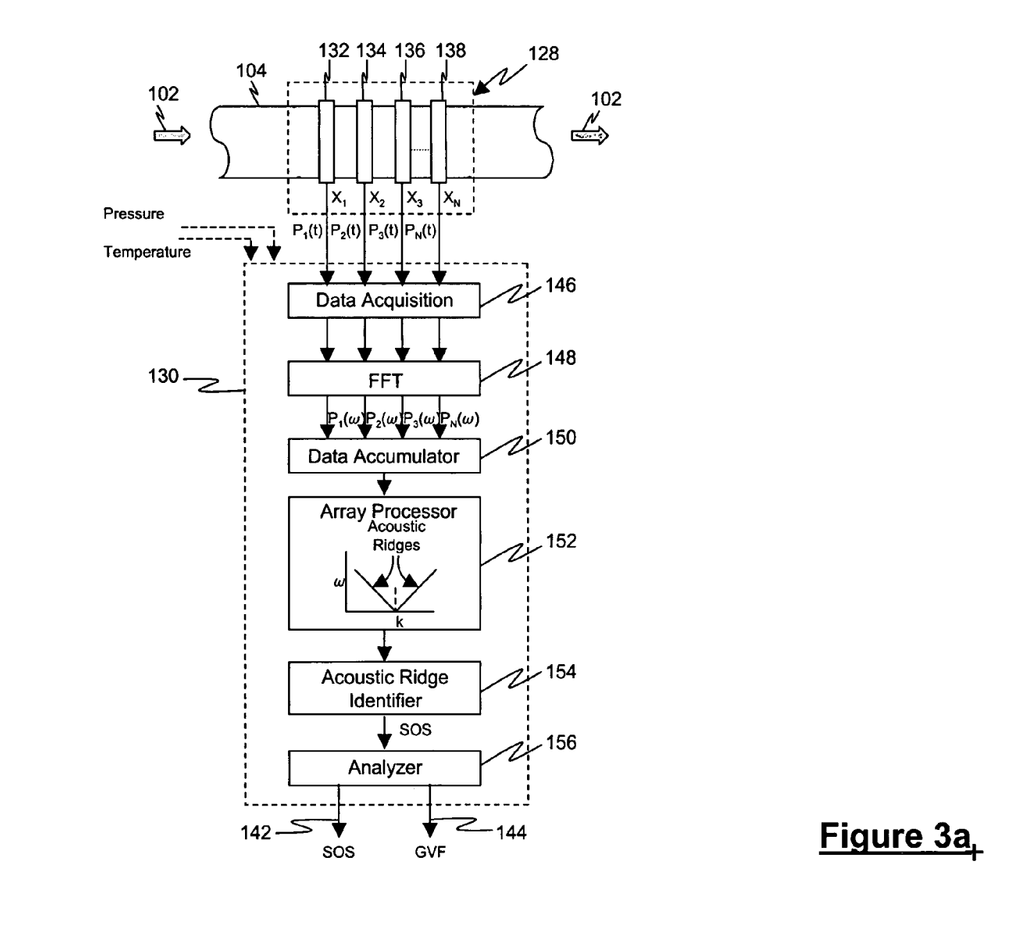
FIG. 3a is a schematic block diagram of a speed of sound meter and accompanying flow logic, in accordance with an exemplary embodiment.

Referring to FIG. 3a, a gas volume fraction (GVF) meter is illustrated, as may be used as the third device 110 in FIG. 1a. The GVF meter 110 may include a sensing device 128 associated with the pipe 104 and a processing unit 130 operably coupled to the sensing device 128. The sensing device 128 may comprise an array of at least two pressure sensors 132,134, located in at least two locations $x_1$, $x_2$ axially along the pipe 104 for sensing respective stochastic signals propagating between the sensors 132,134 within the pipe at their respective locations. Each sensor 132,134 may provide a signal indicating an unsteady pressure at the location of the sensor 132, 134 at each instant in a series of sampling instants. The sensor array may include more than two pressure sensors as depicted by pressure sensors 136, 138 at locations $x_3$, $x_N$, respectively. The array of sensors of the sensing device 128 may include any number of pressure sensors 132-138 greater than two sensors, such as three, four, eight, sixteen or N number of sensors between two and twenty-four sensors. Generally, the accuracy of the measurement improves as the number of sensors in the array increases, wherein the degree of accuracy provided by the greater number of sensors is offset by the increase in complexity and time for computing the desired output parameter of the mixture 102. Therefore, the number of sensors used is dependent at least on the degree of accuracy desired and the desire update rate of the output parameter provided by the apparatus 100. It should be appreciated that the pressure sensors 132-138 may be clamped onto or generally removably mounted to the pipe 104 by any method and or device suitable to the desired end purpose, including a releasable fastener, such as bolts, screws and clamps. Alternatively, the sensors may be permanently attached to, ported in or integral (e.g., embedded) with the pipe 104.

In accordance with the present invention, the apparatus may 100 include at least one acoustic source to enable the measurement of the speed of sound propagating through the mixture ($SOS_M$) for instances of acoustically quiet flow, wherein the at least one acoustic source may be a device the taps or vibrates on the wall of the pipe 104, for example. The at least one acoustic source may be disposed at the input end or output end of the array of sensors 132-138, or at both ends. One should appreciate that in most instances the at least one acoustic source is not necessary and the apparatus 100 may passively detect the acoustic ridge provided in the flow 102, as will be described in greater detail hereinafter. The passive noise includes noise generated by pumps, valves, motors, and the turbulent mixture itself.

Figure 3B:
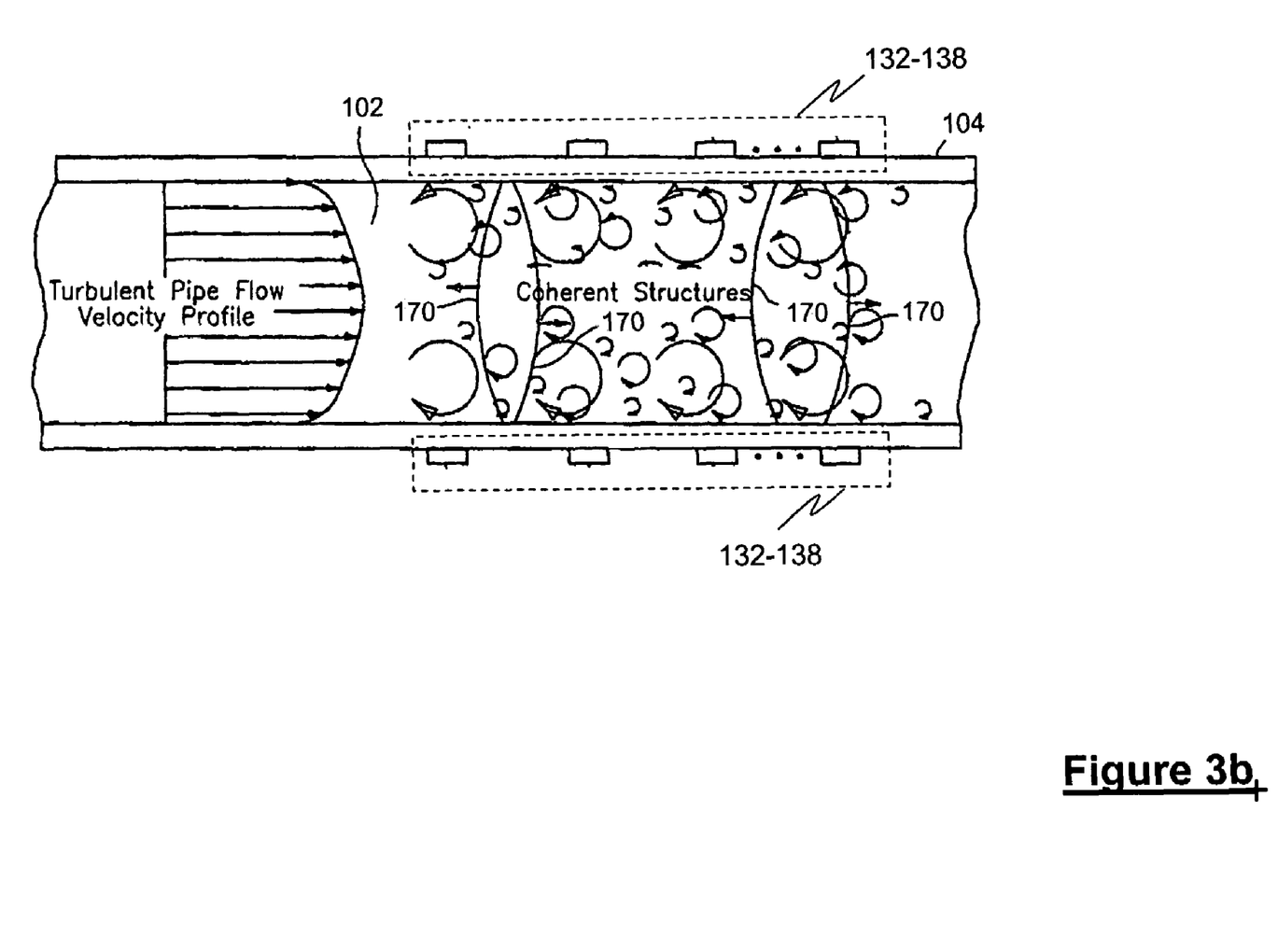
FIG. 3b is a cross-sectional view of a pipe having an aerated fluid flowing within.

The pressure generated by the acoustic pressure disturbances (e.g., acoustic waves 170, see FIG. 3b) may be measured through the pressure sensors 132-138, which provide analog pressure time-varying signals $P_1(t)$, $P_2(t)$, $P_3(t)$, $P_N(t)$ to the signal processing unit 130. The processing unit 130 processes the pressure signals to provide an output signal 142 indicative of the speed of sound propagating through the flow 102, and an output signal 144 indicative of a GVF measurement in response to pressure disturbances generated by acoustic waves propagating through the flow 102. More specifically, the processing unit 130 receives the pressure signals from the array of sensors 132-138 and a data acquisition unit 146 digitizes the pressure signals $P_1(t)$-$P_N(t)$ associated with the acoustic waves propagating through the pipe 104. An FFT logic 148 calculates the Fourier transform of the digitized time-based input signals $P_1(t)$-$P_N(t)$ and provides complex frequency domain (or frequency based) signals $P_1(\omega)$, $P_2(\omega)$, $P_3(\omega)$, $P_N(\omega)$ indicative of the frequency content of the input signals.

Figure 4:
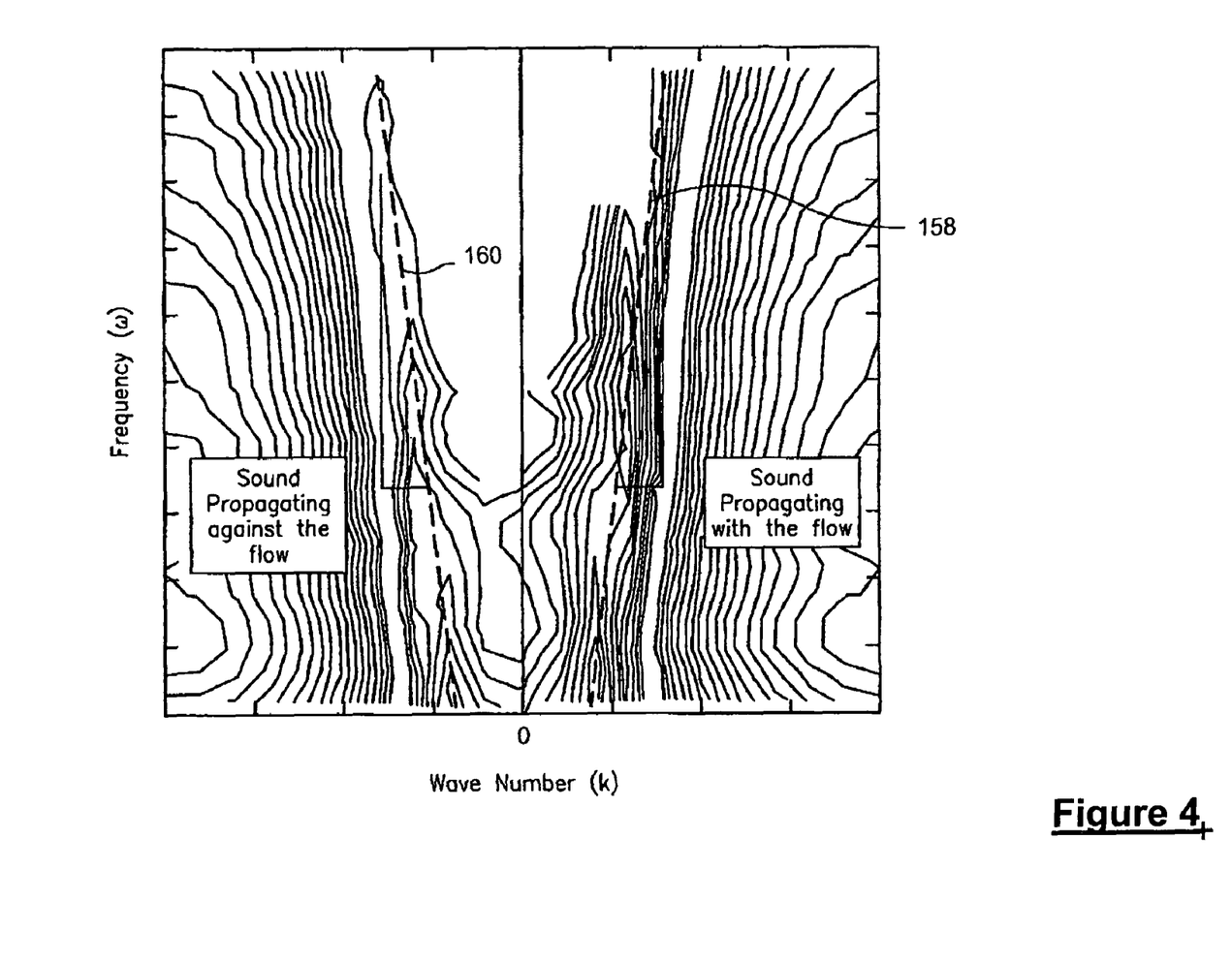
FIG. 4 is a k-ω plot of data processed from an array of pressure sensors use to measure the speed of sound of a fluid flow passing in a pipe embodying the present invention.

A data accumulator 150 accumulates the additional signals $P_1(t)$-$P_N(t)$ from the sensors 132-138, and provides the data accumulated over a sampling interval to an array processor 152, which performs a spatial-temporal (two-dimensional) transform of the sensor data, from the x-t domain to the k-ω domain, and then calculates the power in the k-ω plane, as represented by the k-ω plot shown in FIG. 4. To calculate the power in the k-ω plane, as represented by the k-ω plot in FIG. 4, of either the signals or the differenced signals, the array processor 152 determines the wavelength and so the (spatial) wavenumber k, and also the (temporal) frequency and so the angular frequency ω, of various spectral components of the stochastic parameter. There are numerous algorithms available in the public domain to perform the spatial/temporal decomposition of arrays of sensor units 132-138. In the case of suitable acoustic waves being present in both axial directions, the power in the k-ω plane shown in the k-ω plot of FIG. 4 so determined will exhibit a structure that is called an acoustic ridge 158, 160 in both the left and right planes of the plot respectively, wherein one of the acoustic ridges 158 is indicative of the speed of sound traveling in one axial direction and the other acoustic ridge 160 being indicative of the speed of sound traveling in the other axial direction. The acoustic ridges 158, 160 represent the concentration of a stochastic parameter that propagates through the flow 102 and is a mathematical manifestation of the relationship between the spatial variations and temporal variations described hereinabove. Such a plot will indicate a tendency for k-ω pairs to appear more or less along a line 158, 160 with some slope, wherein the slope is indicative of the speed of sound.

The power in the k-ω plane so determined is then provided to an acoustic ridge identifier 154, which uses one or another feature extraction method to determine the location and orientation (slope) of any acoustic ridge present in the left and right k-ω planes. The velocity may then be determined by using the slope of one of the two acoustic ridges 158, 160 or by averaging the slopes of the acoustic ridges 158, 160. Finally, information including the acoustic ridge orientation (slope) is used by an analyzer 156 to determine the flow parameters relating to the measured speed of sound, such as the consistency or composition of the flow 102, the density of the flow 102, the average size of particles in the flow 102, the air/mass ratio of the flow 102, the gas volume fraction of the flow 102, the speed of sound propagating through the flow 102, and/or the percentage of entrained air within the flow 102.

It should be appreciated that the array processor 152 may use standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by:

$$k=2\pi/\lambda; \quad\quad\quad\quad (\text{Eqn. 4})$$

wherein λ is the wavelength of a spectral component, and the corresponding angular frequencies are given by ω=2πν. One such technique of determining the speed of sound propagating through the flow 102 involves using array processing techniques to define an acoustic ridge 158, 160 in the k-ω plane as shown in FIG. 4. The slope of the acoustic ridge 158, 160 is indicative of the speed of sound propagating through the flow 102. The speed of sound (SOS) is determined by applying sonar arraying processing techniques to determine the speed at which the one dimensional acoustic waves propagate past the axial array of unsteady pressure measurements distributed along the pipe 104. The apparatus 100 of the present invention measures the speed of sound (SOS) of one-dimensional sound waves propagating through the mixture 102 to determine the gas volume fraction of the mixture 102. It is known that sound propagates through various mediums at various speeds in such fields as SONAR and RADAR fields. As such, the speed of sound propagating through the pipe 104 and flow 102 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004; U.S. patent application Ser. No. 09/997,221, filed Nov. 28, 2001, now U.S. Pat. No. 6,587,798; U.S. patent application Ser. No. 10/007,749, filed Nov. 7, 2001, and U.S. patent application Ser. No. 10/762,410, filed Jan. 21, 2004, each of which are incorporated herein by reference.

While the sonar-based flow meter 110 using an array of sensors 132-138 to measure the speed of sound of an acoustic wave propagating through the mixture 102 is shown and described, one will appreciate that any means for measuring the speed of sound of the acoustic wave may used to determine the entrained gas volume fraction of the mixture/fluid 102 or other characteristics of the flow 102 described hereinbefore. The analyzer 156 of the processing unit 130 provides at least one output signal indicative of characteristics of the process flow 102 that are related to the measured speed of sound (SOS) propagating through the flow 102. For example, to determine the gas volume fraction (or phase fraction), the analyzer 156 assumes a nearly isothermal condition for the flow 102. As such the gas volume fraction or the void fraction is related to the speed of sound by the following quadratic equation:

$$Ax^2+Bx+C=0; \quad\quad\quad\quad (\text{Eqn. 5})$$

Wherein, x is the speed of sound, $A=1+rg/rl*(K_{eff}/P-1)-K_{eff}/P$, $B=K_{eff}/P-2+rg/rl$, $C=1-K_{eff}/rl*a_{meas}{}^2)$, Rg=gas density, rl=liquid density, $K_{eff}$=effective K (modulus of the liquid and pipewall), P=pressure and $a_{meas}$=measured speed of sound. Thus, effectively:

$$\text{Gas Volume Fraction (GVF)}=(-B+\text{sqrt}(B^2-4*A*C))/(2*A). \quad\quad (\text{Eqn. 6})$$

Alternatively, the sound speed of the mixture 102 can be related to the volumetric phase fraction (φ_i) of the components and the sound speed (a) and densities (ρ) of the component through the Wood equation as follows:

$$\frac{1}{\rho_{mix} a_{mix\infty}^2} = \sum_{i=1}^{N} \frac{\phi_i}{\rho_i a_i} \text{ where,} \quad\quad (\text{Eqn. 7})$$

$$\rho_{mix} = \sum_{i=1}^{N} \rho_i \phi_i$$

For example, the measured density ($\rho_{mix}$) from the first device 106 (e.g., Coriolis meter or gamma densitometer) may be used as an input to this equation.

Furthermore, one dimensional compression waves propagating within the flow 102 contained within the pipe 104 exert an unsteady internal pressure loading on the pipe 104. The degree to which the pipe 104 displaces as a result of the unsteady pressure loading influences the speed of propagation of the compression wave. The relationship among the infinite domain speed of sound and density of a mixture, the elastic modulus (E), thickness (t), and radius (R) of a vacuum-backed cylindrical conduit, and the effective propagation velocity ($a_{eff}$) for one dimensional compression may then be given by the following expression:

$$a_{eff} = \frac{1}{\sqrt{1/a_{mix\infty}^2 + \rho_{mix}\frac{2R}{Et}}} \quad\quad (\text{Eqn. 8})$$

The mixing rule essentially states that the compressibility of a mixture (1/(ρ a²)) is the volumetrically-weighted average of the compressibilities of the components. Thus, for a gas/liquid mixture at pressure and temperatures typical of paper and pulp industry, the compressibility of the gas phase is orders of magnitudes greater than that of the liquid phase. As such, the compressibility of the gas phase and the density of the liquid phase primarily determine the mixture sound speed making it necessary to have a good estimate of process pressure to interpret the mixture sound speed in terms of the volumetric fraction of entrained gases. The effect of process pressure on the relationship between the sound speed and the entrained air volume fraction is as shown in FIG. 5.

It should be appreciated that some or all of the functions within the processing unit 130 may be implemented in software (using a microprocessor or computer) and/or firmware, or may be implemented using analog and/or digital hardware, having sufficient memory, interfaces, and capacity to perform the functions described herein. In one embodiment of the present invention as shown in FIG. 3a, each of the pressure sensors 132-138 may include a piezoelectric film sensor to measure the unsteady pressures of the fluid flow 102 using either technique described hereinbefore. The piezoelectric film sensors include a piezoelectric material or film to generate an electrical signal proportional to the degree that the material is mechanically deformed or stressed. The piezoelectric sensing element is typically conformed to allow complete or nearly complete circumferential measurement of induced strain to provide a circumferential-averaged pressure signal. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc.

Piezoelectric film ("piezofilm"), like piezoelectric material, is a dynamic material that develops an electrical charge proportional to a change in mechanical stress. Consequently, the piezoelectric material measures the strain induced within the pipe 104 due to unsteady pressure variations (e.g., acoustic waves) within the process mixture 102. Strain within the pipe 104 is transduced to an output voltage or current by the attached piezoelectric sensor. The piezoelectrical material or film may be formed of a polymer, such as polarized fluoropolymer, polyvinylidene fluoride (PVDF). The piezoelectric film sensors are similar to that described in U.S. patent application Ser. Nos. 10/712,818, 10/712,833, and 10/795,111, which are incorporated herein by reference.

Moreover, another embodiment of the present invention may include a pressure sensor such as pipe strain sensors, accelerometers, velocity sensors or displacement sensors, discussed hereinafter, that are mounted onto a strap to enable the pressure sensor to be clamped onto the pipe 104. The sensors may be removable or permanently attached via known mechanical techniques such as mechanical fastener, spring loaded, clamped, clam shell arrangement, strapping or other equivalents. For these certain types of pressure sensors, it may be desirable for the pipe 104 to exhibit a certain amount of pipe compliance. Instead of single point pressure sensors 118-121, at the axial locations along the pipe 12, two or more pressure sensors may be used around the circumference of the pipe 12 at each of the axial locations. The signals from the pressure sensors around the circumference at a given axial location may be averaged to provide a cross-sectional (or circumference) averaged unsteady acoustic pressure measurement. Other numbers of acoustic pressure sensors and annular spacing may be used. Averaging multiple annular pressure sensors reduces noises from disturbances and pipe vibrations and other sources of noise not related to the one-dimensional acoustic pressure waves in the pipe 12, thereby creating a spatial array of pressure sensors to help characterize the one-dimensional sound field within the pipe 12.

The pressure sensors 132-138 of FIG. 3a described herein may be any type of pressure sensor, capable of measuring the unsteady (or ac or dynamic) pressures within the pipe 104, such as piezoelectric, optical, capacitive, resistive (e.g., Wheatstone bridge), accelerometers (or geophones), velocity measuring devices, displacement measuring devices, etc. If optical pressure sensors are used, the sensors 132-138 may be Bragg grating based pressure sensors, such as that described in U.S. patent application, Ser. No. 08/925,598, entitled "High Sensitivity Fiber Optic Pressure Sensor For Use In Harsh Environments", filed Sep. 8, 1997, now U.S. Pat. No. 6,016,702, and in U.S. patent application, Ser. No. 10/224,821, entitled "Non-Intrusive Fiber Optic Pressure Sensor for Measuring Unsteady Pressures within a Pipe", which are incorporated herein by reference. In an embodiment of the present invention that utilizes fiber optics as the pressure sensors 132-138, the pressure sensors 132-138 may be connected individually or they may be multiplexed along one or more optical fibers using wavelength division multiplexing (WDM), time division multiplexing (TDM), or any other optical multiplexing techniques.

In certain embodiments of the present invention, a piezoelectronic pressure transducer may be used as one or more of the pressure sensors 132-138 and it may measure the unsteady (or dynamic or ac) pressure variations inside the pipe or tube 104 by measuring the pressure levels inside of the tube 104, wherein these sensors 132-138 may be ported within the pipe 104 to make direct contact with the mixture 102. In an embodiment of the present invention, the sensors 132-138 may comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors 132-138 may incorporate a built-in MOSFET microelectronic amplifier to convert the high-impedance charge output into a low-impedance voltage signal and the sensor may be powered from a constant-current source and may operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. Furthermore, a data acquisition system of the present invention may incorporate constant-current power for directly powering integrated circuit piezoelectric sensors. Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

It should be appreciated that the output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal. It is also within the scope of the present invention that any strain sensing technique(s) may be used to measure the variations in strain in the pipe 104, such as highly sensitive piezoelectric, electronic or electric, strain gages and piezo-resistive strain gages attached to the pipe 104. Other strain gages include resistive foil type gages having a race track configuration similar to that disclosed U.S. patent application Ser. No. 09/344,094, filed Jun. 25, 1999, now U.S. Pat. No. 6,354,147, which is incorporated in its entirety herein by reference. The present invention also contemplates strain gages being disposed about a predetermined portion of the circumference of the pipe 104, wherein the axial placement of and separation distance $_\Delta X_1$, $_\Delta X_2$, between the strain sensors may be determined as described hereinbefore.

It is also considered within the scope of the present invention that any other strain sensing technique may be used to measure the variations in strain in the tube 104, such as highly sensitive piezoelectric, electronic or electric, strain gages attached to or embedded in the tube 104. While a number of sensors have been described, one will appreciate that any sensor that measures the speed of sound propagating through the fluid 102 may be used with the present invention, including ultrasonic sensors. The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein. Moreover, it should be appreciated that, unless stated otherwise herein, any of the features, characteristics, alternatives or modifications described regarding a particular embodiment herein may also be applied, used, or incorporated with any other embodiment described herein. Also, the drawings herein are not drawn to scale. Although the invention has been described and illustrated with respect to exemplary embodiments thereof, the foregoing and various other additions and omissions may be made therein and thereto without departing from the spirit and scope of the present invention.

What is claimed is:

1. An apparatus for performing a fiscal measurement of at least one characteristic of an aerated fluid flowing within a pipe, the apparatus comprising:
    at least one metering device for determining the mixture density of the fluid, the speed of sound of the fluid and the speed of sound of the liquid portion of the fluid, wherein said at least one metering device generates meter data responsive to said mixture density of the fluid, said speed of sound of the fluid and said speed of sound of the liquid portion of the fluid; and
    a processing device communicated with said at least one metering device, wherein said processing device receives said meter data and processes said meter data to generate the at least one fiscal measurement.

2. The apparatus of claim 1, wherein said at least one metering device includes at least one of a density meter, a speed of sound meter and an Ultra-Sonic flow meter.

3. The apparatus of claim 1, wherein said at least one metering device includes a density meter, said density meter being at least one of a Coriolis meter and a nuclear densitometer.

4. The apparatus of claim 1, wherein said at least one metering device includes a speed of sound meter, said speed of sound meter being a sonar-based gas volume fraction meter.

5. The apparatus of claim 1, wherein said at least one metering device includes an Ultra-Sonic flow meter, said Ultra-Sonic flow meter being least one of a magmeter, a sonar flow meter and a venturi meter.

6. The apparatus of claim 1, wherein said at least one metering device includes a plurality of sensors disposed external to the pipe for measuring at least one of the mixture density of the fluid, the speed of sound of the fluid and the speed of sound of the liquid portion of the fluid.

7. The apparatus of claim 1, further comprising at least one of a temperature sensing device and a pressure sensing device for measuring at least one of the temperature and pressure of the fluid, respectively.

8. The apparatus of claim 1, further comprising a mixing device, wherein said mixing device is associated with the fluid flowing within the pipe, wherein said mixing device is disposed upstream of said at least one metering device.

9. A method for determining a fiscal measurement of at least one characteristic of an aerated fluid flowing within a pipe, the method comprising:
    receiving sensor data responsive to the mixture density of the fluid, the speed of sound of the fluid, the speed of sound of the liquid portion of the fluid and the volumetric flow rate of the fluid flowing within the pipe; and
    processing said sensor data to generate the fiscal measurement of the at least one characteristic of the aerated fluid flowing within the pipe.

10. The method of claim 9, wherein said receiving includes measuring said mixture density of the fluid.

11. The method of claim 9, wherein said receiving further includes measuring at least one of the pressure and temperature of the fluid.

12. The method of claim 9, wherein said receiving further includes measuring said speed of sound of the fluid.

13. The method of claim 9, wherein said receiving further includes measuring said speed of sound of the liquid portion of the fluid.

14. The method of claim 9, wherein said processing includes processing said mixture density of the fluid, said speed of sound of the fluid and said speed of sound of the liquid portion of the fluid to generate at least one of Fiscal Gas Volume Fraction data and Fiscal Volumetric Flow Rate data.

15. The method of claim 14, wherein said processing includes calculating said Fiscal Gas Volume Fraction data via, $$a_{MEAS} = \frac{1}{\left\{\left[\phi\frac{P}{RT} + (1-\phi)\rho_L\right]\left(\frac{\phi}{P\gamma} + \frac{(1-\phi)}{\rho_L a_L^2} + \frac{D-t}{Et}\right)\right\}^{0.5}},$$

Wherein,

| | |
|---|---|
| $a_{MEAS}$ = measured sound speed, m/s | $\rho_L$ = measured liquid density, kg/m³ |
| | $a_L$ = measured liquid sound speed, m/s |
| $\Phi$ = gas volume fraction | |
| P = pressure, Pa absolute | D = pipe outside diameter, m |
| T = temperature, deg K | t = pipe wall thickness, m |
| R = gas constant, J/kg-K | E = pipe modulus of elasticity, Pa |
| $\gamma$ = polytropic exponent | |

16. The method of claim 15, wherein said processing further includes determining the measured mixture density via, $$\rho_{mix} = \rho_{liq}(1-\phi) + \rho_{gas}\phi,$$

wherein, $\rho_{mix}$ is the measured mixture density, $\rho_{liq}$ is the measured liquid density, $\phi$ is the Gas Volume Fraction and $\rho_{gas}$ is the measured gas density.

17. The method of claim 14, wherein said processing includes calculating said Fiscal Volumetric Flow Rate data via, $$Q_{liqfiscal} = (1-GVF_{fiscal})Q_{mixture}$$

wherein, $Q_{liqfiscal}$ is the fiscal measurement of the volumetric flow of the liquid portion (or liquid/solid portion) of the mixture 102 and $Q_{mixture}$ is the measured volumetric flow rate.

18. The method of claim 9, wherein said receiving further includes,
   mixing the aerated fluid flowing within the pipe, and
   measuring at least one of said mixture density of the fluid, the pressure of the fluid, the temperature of the fluid, said speed of sound of the fluid and said speed of sound of the liquid portion of the fluid.

\* \* \* \* \*